United States Patent [19]

Gottschlich et al.

[11] Patent Number: 5,232,978

[45] Date of Patent: Aug. 3, 1993

[54] 1-(2-ARYLETHYL)-PYRROLIDINES

[75] Inventors: Rudolf Gottschlich, Reinheim; Karl-August Ackermann, Ober-Ramstadt; Helmut Prücher, Heppenheim; Andrew Barbar, Weiterstadt; Anton Haase, Mühltal; Hartmut Greiner; Gerd Bartoszyk, both of Darmstadt, all of Fed. Rep. of Germany

[73] Assignee: Merck Patent Gesellschaft Mit Beschrankter Haftung, Darmstadt, Fed. Rep. of Germany

[21] Appl. No.: 786,674

[22] Filed: Nov. 1, 1991

Related U.S. Application Data

[63] Continuation-in-part of Ser. No. 455,018, Dec. 22, 1989, abandoned.

[30] Foreign Application Priority Data

Dec. 23, 1988 [DE] Fed. Rep. of Germany ....... 3843469
Oct. 24, 1989 [DE] Fed. Rep. of Germany ....... 3935371
Nov. 2, 1990 [DE] Fed. Rep. of Germany ....... 4034785

[51] Int. Cl.$^5$ ................. C07D 207/12; C07D 207/00; C07D 401/12; C07D 409/12; A61K 31/38; A61K 31/40

[52] U.S. Cl. ................................ 514/422; 514/424; 548/527; 548/541; 548/550; 548/546; 546/343

[58] Field of Search ............... 548/550, 541, 527, 546; 514/422, 424; 546/343

[56] References Cited

U.S. PATENT DOCUMENTS 3,542,807  11/1970  Lunsford et al. .................. 548/541

FOREIGN PATENT DOCUMENTS 0338331  10/1989  European Pat. Off. ............ 548/556
0374756  12/1989  European Pat. Off. .
3935371  10/1989  Fed. Rep. of Germany .
4016865   4/1974  Japan ................. 548/556
0152461   8/1985  Japan ................. 548/556

*Primary Examiner*—David B. Springer
*Attorney, Agent, or Firm*—Millen, White, Zelano & Branigan

[57] ABSTRACT

Novel 1-(2-arylethyl)-pyrrolidines of the formula

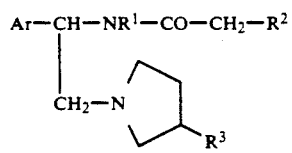

Ar—CH—NR$^1$—CO—CH$_2$—R$^2$    I in which,

Ar is a phenyl group which is unsubstituted or monosubstituted by OH, —O—CO—NH$_2$, —O—CO—NHA, —O—CO—NA$_2$, NH$_2$, —NH—CHO, —NH—CO—A, —NH—CO—NH$_2$, —NH—CO—NHA or NH—SO$_2$—A, R$^1$ is A, R$^2$ is a phenyl, naphthyl, thienyl, benzothienyl or pyridyl group which is unsubstituted or mono- or disubstituted by A, Hal, CF$_3$, OH, OA, —O—CO—NH$_2$, —O—CO—NHA, —O—CO—NA$_2$, NO$_2$, NH$_2$, —NH—CHO, —NH—CO—A, —NH—CO—NH$_2$, —NH—CO—NHA, —NH—SO$_2$A, —CO—A, —CONH$_2$, —CONHA, —CONA$_2$, —CH$_2$—CONH$_2$ and/or —O—CH$_2$—CONH$_2$, R$^3$ is OH or CH$_2$OH, A is alkyl with 1–4 C atoms and Hal is F, Cl, Br or I, or a pharmaceutically acceptable salt thereof for use as an analgesic in humans and veterinary medicine.

12 Claims, No Drawings

1-(2-ARYLETHYL)-PYRROLIDINES

CROSS-REFERENCE TO RELATED APPLICATION

This application is a continuation-in-part of U.S. application Ser. No. 07/455,018, filed on Dec. 22, 1989, now abandoned base German patent applications P 38 43 469.5 of Dec. 23, 1988 and P 39 35 371 of Oct. 24, 1985, all of which applications are entirely incorporated by reference herein.

SUMMARY OF THE INVENTION

The invention relates to a novel 1-(2-arylethyl)pyrrolidines of the formula I

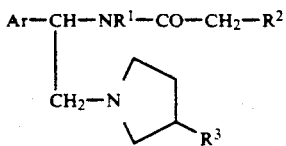

in which
Ar is a phenyl group which is unsubstituted or monosubstituted by OH, —O—CO—NH$_2$, —O—CO—NHA, —O—CO—NA$_2$, NH$_2$, —NH—CHO, —NH—CO—A, —NH—CO—NH$_2$, —NH—CO—NHA or NH—SO$_2$—A,
$R^1$ is A,
$R^2$ is a phenyl, naphthyl, thienyl, benzothienyl or pyridyl group which is unsubstituted or mono- or disubstituted by A, Hal, CF$_3$, OH, OA, —O—CO—NH$_2$, —O—CO—NHA, —O—CO—NA$_2$, NO$_2$, NH$_2$, —NH—CHO, —NH—CO—A, —NH—CO—NH$_2$, —NH—CO—NHA, —NH—SO$_2$A, —CO—A, —CONH$_2$, —CONHA, —CONA$_2$, —CH$_2$—CONH$_2$ and/or —O—CH$_2$—CONH$_2$,
$R^3$ is OH or CH$_2$OH,
A is alkyl with 1-4 C atoms and
Hal is F, Cl, Br or I,
and the salts thereof.

DE-A1-3,935,371 describes compounds of a formula

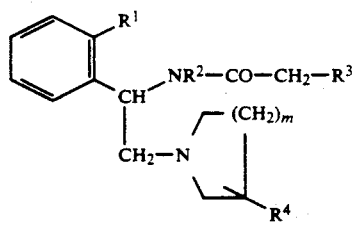

in which $R^1$ can also be H, $R^2$ can also be A, $R^3$ can also be a phenyl, thienyl, naphthyl or benzothienyl group which is unsubstituted or substituted in a particular manner, $R^4$ can also be OH or CH$_2$OH and m can also be 1. However, neither compounds of the above-mentioned formula I nor any individual compounds which are covered by this formula I are described therein. Thus, in view of DE-A1-3,935,371, which is equivalent of copending U.S. Ser. No. 07/455,018, compounds of the formula I are novel and have, by comparison therewith, the nature of a selection invention.

The object of the invention was to find novel compounds with valuable properties, especially those which can be used for the preparation of drugs.

It has been found that the compounds of formula I and their physiologically compatible salts possess valuable pharmacological properties. They exhibit an analgesic action and antagonize inflammation-related hyperalgesia in particular. Thus, the compounds are effective in the writhing test on mice or rats (for method see Siegmund et al., Proc. Soc. Exp. Biol. 95, (1957), 729-731). The analgesic action can also be demonstrated in the tail flick test on mice or rats (for methodology see d'Amour and Smith, J. Pharmacol. Exp. Ther. 72, (1941), 74-79) and in the hot plate test (see Schmauss and Yaksh, J. Pharmacol. Exp. Ther. 228, (1984), 1-12 and the literature cited therein). Especially potent actions are to be observed in rats in the model of carrageenin-induced hyperalgesia (see Bartoszyk and Wild, Neuroscience Letters 101 (1989) 95). In these tests, the compounds show little or no tendency to cause physical dependence. Furthermore, antiinflammatory, antiasthmatic, diuretic, anticonvulsant and/or antitussive actions are apparent which can also be demonstrated by methods commonly used for this purpose. The compounds are moreover suitable for protecting against and treating cerebral oedemas and states of supply deficiency of the central nervous system, especially hypoxia.

The compounds can therefore be used as pharmacological active ingredients in human and veterinary medicine. They are also suitable as intermediates for the preparation of other compounds with valuable properties.

The invention relates to compounds of formula I and to their salts.

The group A is alkyl containing 1, 2, 3 or 4 C especially methyl or ethyl, but also propyl, isopropyl, butyl, isobutyl, sec-butyl or tert-butyl. Accordingly the group OA is preferably methoxy or ethoxy or also propoxy, isopropoxy, butoxy, isobutoxy, secbutoxy or tert-butoxy.

Accordingly, the groups shown below have the preferred meanings specified as follows:
—O—CO—NHA: N-methyl-carbamoyl-oxy, N-ethyl-carbamoyloxy;
—O—CO—NA$_2$: N,N-dimethyl-carbamoyl-oxy, N,N-diethylcarbamoyl-oxy;
—NH—CO—A: Acetamido, propionamido;
—NH—CO—NHA: N'-methyl-ureido, N'-ethyl-ureido;
—NH—SO$_2$-A: Methylsulfonylamino, ethylsulfonylamino;
—CO—A: Acetyl, propionyl;
—CO—NHA: N-methyl-carbamoyl, N-ethyl-carbamoyl;
—CONA$_2$: N'N-dimethyl-carbamoyl, N,N-diethylcarbamoyl.

Hal is preferably Cl, also preferably F, but also Br or I.

Ar is preferably unsubstituted phenyl, also preferably o-, m- or p-aminophenyl, furthermore preferably o-, m- or p-hydroxyphenyl, o-, m- or p-formamidophenyl, o-, m- or p-acetamidophenyl, o-, m- or p-methylsulfonylaminophenyl, o-, m- or p-ureidophenyl, o-, m- or p-N'-methylureidophenyl. Among the substituted phenyl radicals, those in the p position but also those in the m position are preferred.

$R^1$ is preferably methyl.

Particularly preferred $R^2$ radicals are 3,4-dichlorophenyl, o-, m- or p-nitrophenyl, o-, m- or p-aminophenyl, o-, m- or p-formamidophenyl, o-, m- or p-acetamidophenyl, o-, m- or p-ureidophenyl, o-, m- or p-carbamoylmethylphenyl, 1-naphthyl and 4-benzothienyl. However, the $R^2$ radical is preferably also phenyl, o-, m- or p-tolyl, o-, m- or p-ethylphenyl, o-, m- or p-methoxyphenyl, o-, m- or p-ethoxyphenyl, o-, m- or p-hydroxyphenyl, o-, m- or p-fluorophenyl, o-, m- or p-chlorophenyl, o-, m- or p-bromophenyl, o-, m- or p-trifluoromethylphenyl, o-, m- or p-carbamoyloxy-phenyl, o-, m- or p-N-methylcarbamoyloxy-phenyl, o-, m- or p-N,N-dimethylcarbamoyloxy-phenyl, o-, m- or p-N'-methylureido-phenyl, o-, m- or p-methylsulfonylamino-phenyl, o-, m- or p-acetyl-phenyl, o-, m- or p-carbamoylphenyl, o-, m- or p-N-methylcarbamoyl-phenyl, o-, m- or p-N,N-dimethyl-carbamoyl-phenyl, o-, m- or p-carbamoylmethyl-phenyl, o-, m- or p-carbamoylmethoxy-phenyl, 2,3-, 2,4-, 2,5-, 2,6-, 3,4- or 3,5-dimethylphenyl, 2,3-, 2,4-, 2,5-, 2,6-, 3,4- or 3,5-dimethoxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-amino-3-chlorophenyl, 2-amino-4-chlorophenyl, 2-amino-5-chlorophenyl, 2-amino-6-chlorophenyl, 3-amino-2-chlorophenyl, 3-amino-4-chlorophenyl, 3-amino-5-chlorophenyl, 3-amino-6-chlorophenyl, 4-amino-2-chlorophenyl, 4-amino-3-chlorophenyl, 2-amino-3-, -4-, -5- or -6-bromophenyl, 3-amino-2-, -4-, -5- or -6-bromophenyl, 4-amino-2- or -3-bromophenyl, 2-chloro-4-hydroxyphenyl, 3-chloro-4-hydroxyphenyl, 2-hydroxy-4-chlorophenyl, 3-hydroxy-4-chlorophenyl, 3-chloro-4-carboxymethoxyphenyl, 3-chloro-4-methoxycarbonylmethoxyphenyl, 3-chloro-4-ethoxycarbonylmethoxyphenyl, 2-naphthyl, 2-, 3-, 4-, 5-, 6-, 7- or 8-chloro-1-naphthyl, 2- or 3-thienyl, 3-, 4- or 5-chloro-2-thienyl, 3-, 4- or 5-bromo-2-thienyl, 2-, 4- or 5-chloro-3-thienyl, 2-, 4-or 5-bromo-3-thienyl, 3,4-, 3,5- or 4,5-dichloro-2-thienyl, 5-amino-2-thienyl, 5-formamido-2-thienyl, 5-acetamido-2-thienyl, 5-methylsulfonylamino-2-thienyl, 5-ureido-2-thienyl, 5-N,-methylureido-2-thienyl, 2-, 3-, 5-, 6- or 7-benzothienyl, 2-, 3- or 4-pyridyl,3-amino-4-pyridyl, 3-formamido-4-pyridyl, 3-acetamido-4-pyridyl, 3-methylsulfonylamino-4-pyridyl, 3-ureido-4-pyridyl, 3-N'-methylureido-4-pyridyl, 3-amino-4-methyl-2-pyridyl, 3-formamido-4-methyl-2-pyridyl, 3-acetamido-4-methyl-2-pyridyl, 4-methyl-3-methylsulfonylamino-2-pyridyl, 4-methyl-3-ureido-2-pyridyl, 4-methyl-3-N'-methylureido-2-pyridyl, 5-amino-4-methyl-3-pyridyl, 5-formamido-4-methyl-2-pyridyl, 5-acetamido-4-methyl-2-pyridyl, 4-methyl-5-methylsulfonylamino-2-pyridyl, 4-methyl-5-ureido-2-pyridyl, 4-methyl-5-N'-methylureido-2-pyridyl.

$R^3$ is preferably OH, but also $CH_2OH$.

The invention specifically relates to compounds of the formulae Ia and Ib in which the radicals not defined in detail have the meanings indicated for formula I but in which $R^3$ in Ia is OH and $R^3$ in Ib is $CH_2OH$.

The invention relates in particular to those compounds of formulae I, Ia and Ib in which at least one of said radicals has one of the preferred meanings indicated above. Some preferred groups of compounds can be expressed by partial formulae I' and Ia' and Ib', which have formulae I (and Ia and Ib) and wherein the radicals not described more precisely are as defined for formula I, but wherein $R^2$ is phenyl, tolyl, methoxyphenyl, hydroxyphenyl, fluorophenyl, chlorophenyl, bromophenyl, dichlorophenyl, aminochlorophenyl, aminobromophenyl, chlorohydroxyphenyl, nitrophenyl, aminophenyl, ureidophenyl, carbamoylmethylphenyl, carbamoylphenyl, carbamoylmethoxyphenyl, formamidophenyl, acetamidophenyl, methylsulfonamidophenyl,N'-methylureidophenyl,N-methylcarbamoylphenyl, naphthyl, thienyl, benzothienyl or pyridyl.

Other preferred compounds are those of formulae I" and Ia" and Ib", which have formulae I and Ia and Ib, but wherein $R^2$ is dichlorophenyl, aminochlorophenyl, aminobromophenyl, nitrophenyl, aminophenyl, acetamidophenyl or ureidophenyl.

Other preferred compounds are those of formulae I''' and Ia''' and Ib''', which have formulae I and Ia and Ib, but wherein $R^2$ is 3,4-dichlorophenyl, o- or p-nitrophenyl, o- or p-aminophenyl, o- or p-acetamidophenyl or o- or p-ureidophenyl.

Particularly preferred compounds of the formulae I, Ia, Ib, I', Ia', Ib', I", Ia", Ib", I''', Ia''' and Ib''' are those in which Ar is an unsubstituted phenyl group.

Furthermore, preferred compounds amongst all those mentioned are those in which $R^1$ is methyl.

The invention also relates to a process for preparing 1-(2-phenylethyl)-pyrrolidines of the formula I according to claim 1, and the salts thereof, characterized in that a compound of the formula II

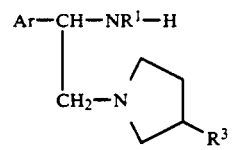

in which Ar, $R^1$ and $R^3$ have the meaning stated for formula I, is reacted with a compound of the formula III

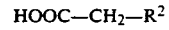

in which $R^2$ has the meaning stated for formula I, or with one of its functional derivatives, or in that a compound which otherwise corresponds to the formula I but contains in place of one or more H atoms one or more groups which can be reduced or eliminated by hydrogenolysis and/or C—C and/or C—N bonds, is treated with a reducing agent, or in that, for the preparation of a compound of the formula I which contains an amide group, a corresponding carboxylic acid or one of its esters is reacted with ammonia or with an amine of the formulae $A-NH_2$ or $A_2NH$, and/or in that one or more of the radicals Ar and/or $R^2$ in a compound of the formula I are converted into one or more other radicals Ar and/or $R^2$, and/or in that a base of the formula I is converted by treatment with an acid into one of its salts.

The compounds of formula I are normally prepared by methods known per se, as described in the literature (e.g. in the standard works such as Houben-Weyl, Methoden der Organischen Chemie (Methods of Organic Chemistry), Georg-Thieme-Verlag, Stuttgart), i.e. under reaction conditions which are known and suitable for said reactions. It is also possible to use variants which are known per se and are not mentioned in further detail here.

The starting materials are generally known or can be prepared analogously to known substances by processes known per se. If desired, they can also be formed in situ in a manner such that they are not isolated from the reaction mixture, but immediately reacted further to give the compounds of formula I. On the other hand, the reaction can be carried out in steps, in which case it is possible to isolate other intermediates.

The individual process variants are illustrated in further detail below.

The compounds of formula I can preferably be prepared by reacting the compounds of formula II with carboxylic acids of formula III or their functional derivatives. Suitable functional derivatives of the compounds of formula III are especially the corresponding esters, in particular the methyl or ethyl esters, and the halides, anhydrides, azides or nitriles, the chlorides being preferred.

Compounds of the formula II can be obtained, for example, by reacting α-alkanoylamino-phenylacetic acids (in which the alkanoyl group has 1–4 C atoms; e.g. α-formamido-phenylacetic acid) with 3-$R^3$-pyrrolidines (3-hydroxpyrrolidine or 3-hydroxymethylpyrrolidine) to give the corresponding 3-$R^3$-pyrrolidides and subsequent simultaneous reduction of the two amide groups with LiAlH$_4$.

Typical compounds of the formula II are, for example, 1-(2-methyl-, 1-(2-ethyl-, 1-(2-propyl-, -(2-isopropyl- or 1-(2-butylamino-2-phenyl-ethyl)-3-hydroxy-pyrrolidine, 1-(2-methyl-, 1-(2-ethyl-, 1-(2-propyl-, (1-(2-isopropyl- or (1-(2-butylamino-2-phenyl-ethyl)-3-hydroxymethyl-pyrrolidine.

Typical compounds of formula III are e.g. phenyltyl chloride, bromide and azide, methyl and ethyl phenylacetate, phenylacetic anhydride, phenylacetonitrile and the corresponding derivatives of 3,4-dichlorophenylacetic acid (e.g. 3,4-dichlorophenylacetyl chloride), of 1-naphthylacetic acid (e.g. 1-naphthylacetyl chloride), of 4-benzothienylacetic acid (e.g. 4-benzothienylacetyl chloride) and o-, m- or p-nitrophenylacetic acid (e.g. o-, m- or p-nitrophenylacetyl chloride).

The reaction of II with III or derivatives of III is conveniently carried out in the presence or absence of an inert organic solvent, e.g. a halogenated hydrocarbon such as methylene chloride, chloroform or trichloroethene, an alcohol such as methanol, ethanol or butanol, an ether such as tetrahydrofuran (THF) or dioxane, an amide such as dimethylformamide (DMF), or a sulfoxide such as dimethyl sulfoxide (DMSO), and/or in the presence or absence of a condensation agent, e.g. a base, at temperatures in the range from −20° to 200°, preferably from 0° to 100°. Examples of suitable bases are alkali metal hydroxides such as NaOH or KOH, alkali metal carbonates such as Na$_2$CO$_3$ or K$_2$CO$_3$, and tertiary amines such as triethylamine or pyridine. Methylene chloride and triethylamine are especially preferred as the solvent and base respectively.

Suitable starting materials for the preparation of compounds of formula I by reducing corresponding compounds which instead of H atoms contain one or more additional reducible or hydrogenolytically cleavable groups and/or C-C bonds and/or C-N bonds are, in particular, compounds of formula IV

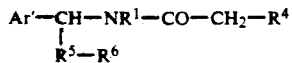

IV in which
Ar' is (a) Ar, (b) a radical which otherwise corresponds to Ar but which contains in place of the H atom of an OH group or of an NH$_2$ group a radical which can be eliminated by hydrogenolysis, or in place of an NH$_2$ group an NO$_2$ group, $R^{1'}$ is (a) $R^1$, (b) an oxo-alkyl group with 1–4 C atoms, $R^4$ is (a) $R^2$, (b) a radical which otherwise corresponds to R but which contains in place of the H atom of an OH group or of an NH$_2$ group a radical which can be eliminated by hydrogenolysis, $R^5$ is (a) —CH$_2$—, (b) —CO— and $R^6$ is (a) 3-$R^3$-pyrrolidino, (b) 3-oxo-pyrrolidino, 3-formylpyrrolidino or 2-, 4- or 5-oxo-3-$R^3$-pyrrolidino;

but where IV must be different from I, i.e. the radicals Ar', $R^{1'}$, $R^4$, $R^5$ and $R^6$ cannot at the same time each have the meanings indicated under (a).

The radical $R^4$ can preferably be o-, m- or p-benzyloxyphenylacetyl.

A suitable reducing agent is preferably hydrogen in the presence of a catalyst, especially a noble metal, nickel or cobalt catalyst. Typical noble metals are, in particular, platinum and palladium, which can be present on supports (e.g. on charcoal, calcium carbonate or strontium carbonate), as oxides (e.g. platinum oxide) or in finely divided form. Nickel and cobalt catalysts are conveniently used as Raney metals. Hydrogenation is conveniently carried out at pressures in the range from about 1 to about 200 bar and at temperatures in the range from about −80° to +150°, preferably from 20° to 100°, in the presence of an inert solvent, e.g. an alcohol such as methanol, ethanol or isopropanol, a carboxylic acid such as acetic acid, an ester such as ethyl acetate, or an ether such as THF or dioxane.

To prepare a compound of the formula I which contains an amide group, that is to say one (or more) of the groups —CONH$_2$, —CONHA or —CONA$_2$, it is possible to react a corresponding carboxylic acid or a corresponding ester, preferably a lower alkyl ester, which contains the group COOA in place of the amide group, with ammonia or an amine of the formulae ANH$_2$ or A$_2$NH. Carboxylic acids are preferably reacted in the presence of a dehydrating agent such as dicyclohexylcarbodiimide or carbonyldiimidazole in an inert solvent such as DMF at 15°–40°.

If desired, one or more of the radicals Ar and/or $R^2$, in a compound of formula I, can be exchanged for one or more different radicals Ar and/or $R^2$.

Thus it is possible to cleave ether groups (e.g. OA groups) to form OH groups, e.g. by treatment with dimethyl sulfide/boron tribromide complex, e.g. in toluene, THF or DMSO, or by fusion with pyridine or aniline hydrohalides, preferably pyridine hydrochloride, at about 150°–250°, or by treatment with diisobutylaluminium hydride in toluene at about 0°–110°.

It is also possible to etherify OH groups, e.g. by first preparing the corresponding alkali metal (e.g. Na or K) alcoholates, phenolates or salts and then reacting these with appropriate halogen compounds, e.g. with alkyl halides such as methyl chloride, bromide or iodide, chloroacetamide or bromoacetamide, conveniently in the presence of one of the solvents indicated above, at temperatures in the range from 0° to 100°.

Nitro groups can be reduced to amino groups, preferably by catalytic hydrogenation under the abovementioned conditions, e.g. with Raney Ni in methanol or ethanol at 15°–40° and under atmospheric pressure Amino groups can be acylated, e.g. with acid chlorides such as acetyl or methanesulfonyl chloride, or the hemiester chlorides of oxalic acid or succinic acid, preferably in inert solvents such as dichloromethane at 15°–40°. Formylation of amino groups is also possible by reaction with excess formic acid at 80°–100° for several hours. Reaction of primary amino compounds with cyanates, e.g. with KCNO in water at 15°–40°, gives the corresponding ureido compounds; with alkyl isocyanates, e.g. in inert solvents such as THF at 15°–40°, it results in N'-alkyl-ureido compounds correspondingly.

A base of formula I can be converted into the corresponding acid addition salt with an acid. Acids which can be used for this reaction are those producing physiologically compatible salts. Thus it is possible to use inorganic acids, e.g. sulfuric acid, nitric acid, hydrohalic acids such as hydrochloric acid or hydrobromic acid, phosphoric acids such as orthophosphoric acid, and sulfamic acid, or organic acids, in particular aliphatic, alicyclic, araliphatic, aromatic or heterocyclic monobasic or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalenemonosulfonic and naphthalenedisulfonic acids and lauryl sulfuric acid. Salts with physiologically incompatible acids, e.g. picrates, can be used to purify the compounds of formula I.

If desired, the free bases of formula I can be liberated from their salts by treatment with strong bases such as sodium or potassium hydroxide or sodium or potassium carbonate The compounds of formula I contain at least two chiral centres and can therefore exist in racemic or optically active form. Racemates obtained can be mechanically or chemically resolved into the enantiomers by methods known per se. Preferably, diastereoisomers are formed from the racemic mixture by reaction with an optically active resolving agent. Examples of suitable resolving agents are optically active acids such as the D and L forms of tartaric acid, diacetyltartaric acid, dibenzoyltartaric acid, mandelic acid, malic acid or lactic acid, or the various optically active camphorsulfonic acids such as β-camphorsulfonic acid.

It is also advantageous to resolve enantiomers with the help of a column packed with an optically active resolving agent (e.g. dinitrobenzoylphenylglycine); a suitable eluent is e.g. a mixture of hexane/isopropanol/acetonitrile, e.g. in a volume ratio of 82:15:3.

Naturally it is also possible to obtain optically active compounds of formula I by the methods described above using starting materials (e.g. those of formula II) which are already optically active.

The invention further relates to the use of the compounds of formula I and their physiologically compatible salts for making pharmaceutical preparations, especially by a non-chemical method This can be done by converting them into a suitable dosage form, together with at least one solid, liquid and/or semiliquid carrier or adjunct and, if necessary, in combination with one or more additional active ingredients.

The invention further relates to compositions, especially pharmaceutical preparations, comprising at least one compound of formula I and/or one of its physiologically compatible salts.

These preparations can be used as drugs in human or veterinary medicine Possible carriers are organic or inorganic substances which are suitable for enteral (e.g. oral), parenteral or topical administration and which do not react with the novel compounds, for example water, vegetable oils, benzyl alcohols, alkylene glycols, polyethylene glycols, glycerol triacetate, gelatin, carbohydrates such as lactose or starch, magnesium stearate, talc and petroleum jelly Forms used for oral administration are, in particular, tablets, pills, coated tablets, capsules, powders, granules, syrups, juices or drops, forms used for rectal administration are suppositories, forms used for parenteral administration are solutions, preferably oily or aqueous solutions, as well as suspensions, emulsions or implants, and forms used for topical administration are ointments, creams or powders. The novel compounds can also be lyophilized and the resulting lyophilizates used, e.g., to make injectable preparations. The preparations indicated can be sterilized and/or can contain adjuncts such as lubricants, preservatives, stabilizers and/or wetting agents, emulsifiers, salts for modifying the osmotic pressure, buffer substances, colorants, taste improvers and/or flavorings. If desired, they can also contain one or more additional active ingredients, e.g., one or more vitamins.

The compounds of formula I and their physiologically compatible salts can be used for combating diseases, especially conditions of pain.

Here the substances of the invention are normally administered analogously to known agents. Known analogous agents with respect to administration are: diclofenac or indomethacine (analgesic as well as anti-inflammatory); cromolyn or cromoglicic acid (anti-asthmatic); hydrochlorothiazide (diuretic); carbamazepine (anti-convulsant); and ambroxol (anti-tussive). The substances are administered preferably in dosages of between about 1 and 500 mg, especially of between 5 and 100 mg, per dosage unit. The daily dosage is preferably between about 0.02 and 10 mg/kg of body weight However, the particular dosage for each individual patient depends on a very wide variety of factors, for example efficacy of the particular compound used, age, body weight, general state of health, sex, diet, time and route of administration, rate of excretion, drug combination and severity of the particular disease for which the therapy is intended. Oral administration is preferred. The foregoing dosages apply to the used of the compounds of this invention for all of the purposes mentioned herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application Federal Republic of German P 40 34 785.0, filed Nov. 2, 1990, are hereby incorporated by reference.

In the following Examples, "conventional working-up" means: water or dilute sodium hydroxide solution is added, if necessary, the mixture is extracted with methylene chloride, the phases are separated, the organic phase is dried with sodium sulfate and filtered, the filtrate is evaporated and the residue is purified by chromatography on silica gel and/or by crystallization.

HCl' = hydrochloride. Rf = Rf on thin-layer silica gel 60 $F_{254}$ (E. Merck, Art. No. 5715), $CH_2Cl_2/CH_3OH$ 9:1 with the addition of 0.5% triethylamine. $[\alpha] = [\alpha]^{20}_D$, c = 1 in methanol.

EXAMPLE 1

30 ml of triethylamine are added to a solution of 22 g of 1-(2-methylamino-2-phenyl-ethyl)-3-hydroxypyrrolidine [di-HCl', m.p.201°; obtainable by reaction of α-formamido-phenylacetic acid with 3-hydroxypyrrolidine to give α-formamido-phenylacetic acid 3-hydroxypyrrolidide (oil) and reduction with $LiAlH_4$] in 250 ml of dichloromethane. Subsequently a solution of 22.4 g of 3,4-dichlorophenylacetyl chloride in 200 ml of dichloromethane is added dropwise while stirring, the mixture is then stirred at 20° for 2 h and conventional working-up results in 1-[2-(N-3,4-dichlorophenylacetyl-N-methylamino) -2-phenylethyl]-3-hydroxy-pyrrolidine. Rf 0.37. HCl', m.p. 201°.

EXAMPLE 2

In analogy to Example 1, 1-(2-methylamino-2-phenylethyl)-3-hydroxymethyl-pyrrolidine [obtainable by reduction of α-formamido-phenylacetic acid 3-hydroxymethyl-pyrrolidide with $LiAlH_4$] and 3,4-dichlorophenylacetyl chloride result in 1-[2-(N-3,4-dichlorophenylacetyl-N-methyl-amino)-2-phenylethyl]-3-hydroxymethylpyrrolidine, Rf 0.36. HCl', m.p. 225°.

EXAMPLE 3

In analogy to Example 1, 1-[2-(N-methyl-N-p-nitrophenylacetyl-amino)-2-phenylethyl]-3-hydroxypyrrolidine, Rf 0.34, is obtained with p-nitrophenylacetyl chloride.

α-Formamido-phenylacetic acid 3-hydroxy-pyrrolidide results analogously [via 1-(2-methylamino-2-phenylethyl) -3R-hydroxy-pyrrolidine] in 1-2-N-methyl-N-p-nitrophenylacetylamino)-2-phenyl-ethyl]-3R-hydroxy-pyrrolidine, Rf 0.34; $[\alpha]-2.2°$. HCl', m.p. 235°.

αS-Formamido-phenylaceticacid3-hydroxy-pyrrolidide results analogously [via 1-(2S-methylamino-2-phenylethyl)-3-hydroxy-pyrrolidine] in 1-[2S-(N-methyl-N-p-nitrophenylacetylamino)-2-phenyl-ethyl]-3-hydroxy-pyrrolidine, Rf 0.34.

αS-Formamido-phenylacetic acid 3S-hydroxy-pyrrolidide results analogously [via 1-(2S-methylamino-2-phenyl-ethyl)-3S-hydroxy-pyrrolidine] in 1-[2S-(N-methyl-N-p-nitrophenylacetylamino)-2-phenyl-ethyl]-3S-hydroxy-pyrrolidine, Rf. 0.34.

The following are obtained analogously with o- or m-nitrophenylacetyl chloride:
1-[2-(N-methyl-N-o-nitrophenylacetyl-amino)-2-phenylethyl]-3-hydroxy-pyrrolidine
1-[2-(N-methyl-N-o-nitrophenylacetyl-amino)-2-phenylethyl]-3R-hydroxy-pyrrolidine
1-[2-(N-methyl-N-o-nitrophenylacetyl-amino)-2-phenylethyl]-3S-hydroxy-pyrrolidine
1-[2S-(N-methyl-N-o-nitrophenylacetyl-amino)-2-phenylethyl]-3-hydroxy-pyrrolidine, Rf 0.35
1-[2-(N-methyl-N-m-nitrophenylacetyl-amino)-2-phenylethyl]-3-hydroxy-pyrrolidine
1-[2-(N-methyl-N-m-nitrophenylacetyl-amino)-2-phenylethyl]-3R-hydroxy-pyrrolidine
1-[2-(N-methyl-N-m-nitrophenylacetyl-amino)-2-phenylethyl]-3S-hydroxy-pyrrolidine
1-[2S-(N-methyl-N-m-nitrophenylacetyl-amino)-2-phenylethyl]-3-hydroxy-pyrrolidine.

EXAMPLE 4

The following are obtained in analogy to Example 1 with o-, m- or p-methylphenylacetyl chloride:
1-[2-(N-o-methylphenylacetyl-N-methyl-amino)-2-phenylethyl]-3-hydroxy-pyrrolidine
1-[2-(N-m-methylphenylacetyl-N-methyl-amino)-2-phenylethyl]-3-hydroxy-pyrrolidine
1-[2-(N-p-methylphenylacetyl-N-methyl-amino)-2-phenylethyl]-3-hydroxy-pyrrolidine;
with o-, m- or p-fluorophenylacetyl chloride:
1-[2-(N-o-fluorophenylacetyl-N-methyl-amino)-2-phenylethyl]-3-hydroxy-pyrrolidine
1-[2-(N-m-fluorophenylacetyl-N-methyl-amino)-2-phenylethyl]-3-hydroxy-pyrrolidine
1-[2-(N-p-fluorophenylacetyl-N-methyl-amino)-2-phenylethyl]-3-hydroxy-pyrrolidine;
with o-, m- or p-chlorophenylacetyl chloride:
1-[2-(N-o-chlorophenylacetyl-N-methyl-amino)-2-phenylethyl]-3-hydroxy-pyrrolidine
1-[2-(N-m-chlorophenylacetyl-N-methyl-amino)-2-phenylethyl]-3-hydroxy-pyrrolidine
1-[2-(N-p-chlorophenylacetyl-N-methyl-amino)-2-phenylethyl]-3-hydroxy-pyrrolidine;
with o-, m- or p-bromophenylacetyl chloride:
1-[2-(N-o-bromophenylacetyl-N-methyl-amino)-2-phenylethyl]-3-hydroxy-pyrrolidine
1-[2-(N-m-bromophenylacetyl-N-methyl-amino)-2-phenylethyl]-3-hydroxy-pyrrolidine
1-[2-(N-p-bromophenylacetyl-N-methyl-amino)-2-phenylethyl]-3-hydroxy-pyrrolidine;
with o-, m- or p-trifluoromethyl-phenylacetyl chloride:
1-[2-(N-methyl-N-o-trifluorophenylacetyl-amino)-2-phenylethyl]-3-hydroxy-pyrrolidine
1-[2-(N-methyl-N-m-trifluorophenylacetyl-amino)-2-phenylethyl]-3-hydroxy-pyrrolidine
1-[2-(N-methyl-N-p-trifluorophenylacetyl-amino)-2-phenylethyl]-3-hydroxy-pyrrolidine;
with o-, m- or p-methoxyphenylacetyl chloride:
1-[2-(N-o-methoxyphenylacetyl-N-methyl-amino)-2-phenylethyl]-3-hydroxy-pyrrolidine
1-[2-(N-m-methoxyphenylacetyl-N-methyl-amino)-2-phenylethyl]-3-hydroxy-pyrrolidine
1-[2-(N-p-methoxyphenylacetyl-N-methyl-amino)-2-phenylethyl]-3-hydroxy-pyrrolidine;
with o-, m- or p-acetylphenylacetyl chloride:
1-[2-(N-o-acetylphenylacetyl-N-methyl-amino)-2-phenylethyl]-3-hydroxy-pyrrolidine
1-[2-(N-m-acetylphenylacetyl-N-methyl-amino)-2-phenylethyl]-3-hydroxy-pyrrolidine
1-[2-(N-p-acetylphenylacetyl-N-methyl-amino)-2-phenylethyl]-3-hydroxy-pyrrolidine;
with o-, m- or p-carbamoylphenylacetyl chloride:
1-[2-(N-o-carbamoylphenylacetyl-N-methyl-amino)-2-phenylethyl]-3-hydroxy-pyrrolidine 1-[2-(N-m-carbamoylphenylacetyl-N-methyl-amino)-2-phenylethyl]-3-hydroxy-pyrrolidine 1-[2-(N-m-carbamoylphenylacetyl-N-methyl-amino)-2-phenylethyl]-3S-hydroxy-pyrrolidine, Rf 0.15

1-[2-(N-p-carbamoylphenylacetyl-N-methyl-amino)-2-phenylethyl]-3-hydroxy-pyrrolidine 1-[2S-(N-p-carbamoylphenylacetyl-N-methyl-amino)-2-phenylethyl]-3S-hydroxy-pyrrolidine, Rf 0.12;

with o-, m- or p-(N-methylcarbamoyl)-phenylacetyl chloride:

1-[2-(N-methyl-N-o-(N-methylcarbamoyl)-phenylacetylamino)-2-phenyl-ethyl]-3-hydroxy-pyrrolidine 1-[2-(N-methyl-N-m-(N-methylcarbamoyl)-phenylacetylamino)-2-phenyl-ethyl]-3-hydroxy-pyrrolidine 1-[2-(N-methyl-N-p-(N-methylcarbamoyl)-phenylacetylamino)-2-phenyl-ethyl-]-3-hydroxy-pyrrolidine;

with o-, m- or p-(N,N-dimethylcarbamoyl)-phenylacetyl chloride:

1-[2-(N-o-(N,N-dimethylcarbamoyl)-phenylacetyl-N-methylamino)-2-phenyl-ethyl]-3-hydroxy-pyrrolidine 1-[2-(N-p-(N,N-dimethylcarbamoyl)-phenylacetyl-N-methylamino)-2-phenyl-ethyl]-3-hydroxy-pyrrolidine 1-[2-(N-m-(N,N-dimethylcarbamoyl)-phenylacetyl-N-methylamino)-2-phenyl-ethyl]-3-hydroxy-pyrrolidine;

with o-, m- or p-carbamoylmethyl-phenylacetyl chloride:

1-[2-(N-o-carbamoylmethyl-phenylacetyl-N-methyl-amino)-2-phenyl-ethyl]-3-hydroxy-pyrrolidine 1-[2-(N-m-carbamoylmethyl-phenylacetyl-N-methyl-amino)-2-phenyl-ethyl]-3-hydroxy-pyrrolidine 1-[2-(N-p-carbamoylmethyl-phenylacetyl-N-methyl-amino)-2-phenyl-ethyl]-3-hydroxy-pyrrolidine 1-[2S-(N-p-carbamoylmethyl-phenylacetyl-N-methyl-amino)-2-phenyl-ethyl]-3S-hydroxy-pyrrolidine, Rf 0.18;

with o-, m- or p-carbamoylmethoxy-phenylacetyl chloride:

1-[2-(N-o-carbamoylmethoxy-phenylacetyl-N-methyl-amino)-2-phenyl-ethyl]-3-hydroxy-pyrrolidine 1-[2-(N-m.-carbamoylmethoxy-phenylacetyl-N-methyl-amino)-2-phenyl-ethyl]-3-hydroxy-pyrrolidine 1-[2-(N-p-carbamoylmethoxy-phenylacetyl-N-methyl-amino)-2phenyl-ethyl]-3-hydroxy-pyrrolidine;

with phenylacetyl chloride:

1-[2-(N-methyl-N-phenylacetyl-amino)-2-phenyl-ethyl]-3-hydroxy-pyrrolidine;

with 1- or 2-naphthylacetyl chloride:

1-[2-(N-methyl-N-(1-naphthylacetyl-amino)-2-phenylethyl]-3-hydroxy-pyrrolidine

1-[2-(N-methyl-N-(2-naphthylacetyl-amino)-2-phenylethyl]-3-hydroxy-pyrrolidine;

with 2- or 3- thienylocethyl chloride;

1-[2-(N-methyl-N-(2-thienylacetyl-amino)-2-phenyl-ethyl]3-hydroxy-pyrrolidine

1-[2-(N-methyl-N-(3-thienylacetyl-amino)-2-phenyl-ethyl]3-hydroxy-pyrrolidine;

with 4-benzothienyl-acetyl chloride:

1-[2-(N-(4-benzothienylacetyl-N-methyl-amino)-2-phenylethyl]-3-hydroxy-pyrrolidine;

with 2-, 3- or 4-pyridylacetyl chloride:

1-[2-(N-methyl-N-(2-pyridyl)-acetyl-amino)-2-phenylethyl]-3-hydroxy-pyrrolidine

1-[2-(N-methyl-N-(3-pyridyl)-acetyl-amino)-2-phenylethyl]-3-hydroxy-pyrrolidine

1-[2-(N-methyl-N-(4-pyridyl)-acetyl-amino)-2-phenylethyl]-3-hydroxy-pyrrolidine;

with 5-nitro-2-thienyl-acetyl chloride:

1-[2-(N-methyl-N-(5-nitro-2-thienyl-acetyl)-amino)-2-phenyl-ethyl]-3-hydroxy-pyrrolidine;

with 3-, 4-, 5- or 6-chloro-2-nitrophenylacetyl chloride:

1-[2-(N-3-chloro-2-nitrophenylacetyl-N-methyl-amino)-2-phenyl-ethyl]-3-hydroxy-pyrrolidine 1-[2-(N-4-chloro-2-nitrophenylacetyl-N-methyl-amino)-2-phenyl-ethyl]-3-hydroxy-pyrrolidine 1-[2-(N-5-chloro-2-nitrophenylacetyl-N-methyl-amino)-2-phenyl-ethyl]-3-hydroxy-pyrrolidine 1-[2-(N-6-chloro-2-nitrophenylacetyl-N-methyl-amino)-2-phenyl-ethyl]-3-hydroxy-pyrrolidine;

with 2-, 4-, 5- or 6-chloro-3-nitrophenylacetyl chloride:

1-[2-(N-2-chloro-3-nitrophenylacetyl-N-methyl-amino)-2-phenyl-ethyl]-3-hydroxy-pyrrolidine 1-[2-(N-4-chloro-3-nitrophenylacetyl-N-methyl-amino)-2-phenyl-ethyl]-3-hydroxy-pyrrolidine 1-[2-(N-5-chloro-3-nitrophenylacetyl-N-methyl-amino)-2-phenyl-ethyl]-3-hydroxy-pyrrolidine 1-[2-(N-6-chloro-3-nitrophenylacetyl-N-methyl-amino)-2-phenyl-ethyl]-3-hydroxy-pyrrolidine;

with 2- or 3-chloro-4-nitrophenylacetyl chloride:

1-[2-(N-2-chloro-4-nitrophenylacetyl-N-methyl-amino)-2-phenyl-ethyl]-3-hydroxy-pyrrolidine;

1-[2-(N-3-chloro-4-nitrophenylacetyl-N-methyl-amino)-2-phenyl-ethyl]-3-hydroxy-pyrrolidine;

with 3-, 4-, 5- or 6-bromo-2-nitrophenylacetylchloride:

1-[2-(N-3-bromo-2-nitrophenylacetyl-N-methyl-amino)-2-phenyl-ethyl]-3-hydroxy-pyrrolidine 1-[2-(N-4-bromo-2-nitrophenylacetyl-N-methyl-amino)-2-phenyl-ethyl]-3-hydroxy-pyrrolidine 1-[2-(N-5-bromo-2-nitrophenylacetyl-N-methyl-amino)-2-phenyl-ethyl]-3-hydroxy-pyrrolidine 1-[2-(N-6-bromo-2-nitrophenylacetyl-N-methyl-amino)-2-phenyl-ethyl]-3-hydroxy-pyrrolidine;

with 2-, 4-, 5- or 6-bromo-3-nitrophenylacetyl chloride

1-[2-(N-2-bromo-3-nitrophenylacetyl-N-methyl-amino)-2-phenyl-ethyl]-3-hydroxy-pyrrolidine 1-[2-(N-4-bromo-3-nitrophenylacetyl-N-methyl-amino)-2-phenyl-ethyl]-3-hydroxy-pyrrolidine 1-[2-(N-5-bromo-3-nitrophenylacetyl-N-methyl-amino)-2-phenyl-ethyl]-3-hydroxy-pyrrolidine 1-[2-(N-6-bromo-3-nitrophenylacetyl-N-methyl-amino)-2-phenyl-ethyl]-3-hydroxy-pyrrolidine;

with 2- or 3-bromo-4-nitrophenylacetyl chloride:

1-[2-(N-2-bromo-4-nitrophenylacetyl-N-methyl-amino)-2-phenyl-ethyl]-3-hydroxy-pyrrolidine 1-[2-(N-3-bromo-4-nitrophenylacetyl-N-methyl-amino)-2-phenyl-ethyl]-3-hydroxy-pyrrolidine.

EXAMPLE 5

6 g of 3-chloro-4-hydroxy-phenylacetohydrazide (obtainable from ethyl 3-chloro-4-hydroxy-phenylacetate with hydrazine) are dissolved in 200 ml of water and 40 ml of 1 N hydrochloric acid and, while stirring at 0°–3°, a solution of 2.4 g of NaNO₂ in 40 ml of water is added dropwise, and the mixture is then stirred for 30 min and the azide which has formed is extracted with dichloromethane. After the solution has been dried over MgSO₄ and concentrated to 50 ml it is added dropwise with stirring to a solution of 6.6 g of 1-(2-methylamino-2-phenyl-ethyl)-3-hydroxy-pyrrolidine and 4.4 ml of triethylamine in 100 ml of dichloromethane. The mixture is then stirred at 20° for 2 h and subjected to conventional working-up, resulting in 1-[2-(N-3-chloro-4-hydroxy-phenylacetyl-N-methyl-amino)  -2-phenyl-ethyl]-3-hydroxypyrrolidine.

EXAMPLE 6

A solution of 1 g of 1-[2-(N-p-benzyloxyphenylacetyl-N -methyl-amino)-2-phenyl-ethyl]-3-hydroxy-pyrrolidine [obtainable from 1-(2-methylamino-2-phenylethyl) -3-hydroxypyrrolidine and p-benzyloxyphenylacetyl chloride] in 25 ml of ethyl acetate is hydrogenated on 0.5 g of 5% Pd-C at 20° and under 1 bar until the hydrogen uptake ceases, then the mixture is filtered and evaporated to result in 1-[2-(N-p-hydroxy-phenylacetyl-N-methyl  -amino)-2-phenyl-ethyl]-3-hydroxy-pyrrolidine.

The following are obtained analogously by hydrogenolysis of the corresponding o- or m-benzyloxy-phenylacetyl derivatives:

1-[2-(N-o-hydroxyphenylacetyl-N-methyl-amino)-2-phenylethyl]-3-hydroxy-pyrrolidine
1-[2-(N-m-hydroxyphenylacetyl-N-methyl-amino)-2-phenylethyl]-3-hydroxy-pyrrolidine.

The following are obtained analogously by hydrogenolysis of 1-[2-(N-methyl-N-m-trifluoromethyl-phenylacetyl-amino)-2-o-, -m- or -p-benzyloxyphenyl-ethyl]3-hydroxy-pyrrolidine:

1-[2-(N-methyl-N-m-trifluoromethyl-phenylacetyl-amino)-o-hydroxyphenyl-ethyl]-3-hydroxy-pyrrolidine
1-[2-(N-methyl-N-m-trifluoromethyl-phenylacetyl-amino)-2-m-hydroxyphenyl-ethyl]-3-hydroxy-pyrrolidine
1-[2-(N-methyl-N-m-trifluoromethyl-phenylacetyl-amino)-2-p-hydroxyphenyl-ethyl]-3-hydroxy-pyrrolidine.

EXAMPLE 7

A solution of 10 g of 1-[2-(N-3-(benzyloxy-carbonyl-amino)-4-pyridyl-acetyl-N-methyl-amino)-2-phenylethyl]-3-hydroxy-pyrrolidine [obtainable from 1-(2-methylamino-2-phenyl-ethyl)-3-hydroxy-pyrrolidine and 3-benzyloxycarbonylamino-4-pyridyl-acetyl chloride] in 250 ml of methanol is hydrogenated on 0.5 g of 5% Pd-C at 20° and under 1 bar until the hydrogen uptake ceases, and the mixture is filtered and evaporated to result in 1-[2-(N-(3-amino-4-pyridyl-acetyl)-N-methyl-amino)-2-phenylethyl]-3-hydroxy-pyrrolidine.

The following are obtained analogously by hydrogenolysis of the corresponding benzyloxycarbonyl derivatives:

1-[2-(N-(3-amino-4-methyl-2-pyridyl-acetyl)-N-methylamino)-2-phenyl-ethyl]-3-hydroxy-pyrrolidine
1-[2-(N-(5-amino-4-methyl-2-pyridyl-acetyl)-N-methylamino)  -2-phenyl-ethyl]-3-hydroxy-pyrrolidine
1-[2-(N-methyl-N-m-trifluoromethylphenylacetyl-amino)-2-o-aminophenyl-ethyl-]-3-hydroxy-pyrrolidine
1-[2-(N-methyl-N-m-trifluoromethylphenylacetyl-amino)-2-m-aminophenyl-ethyl]-3-hydroxy-pyrrolidine
1-[2-(N-methyl-N-m-trifluoromethylphenylacetyl-amino)-2-p-aminophenyl-ethyl]-3-hydroxy-pyrrolidine.

EXAMPLE 8

A mixture of 3.82 g of 1-[2-(N-p-carboxyphenylacetyl-N-methyl-amino)-2-phenyl-ethyl]-3-hydroxypyrrolidine [obtainable by reaction of 1-(2-methylamino-2-phenylethyl)-3-hydroxy-pyrrolidine with 4-methoxycarbonyl-phenylacetyl chloride to give 1-[2-(N-p-methoxycarbonyl-phenylacetyl-N-methyl-amino)  -2-phenyl-ethyl]-3-hydroxy-pyrrolidine and subsequent hydrolysis], 1.62 g of carbonyldiimidazole and 140 ml of DMF is stirred at 20° for 1 h. 15 ml of aqueous NH3 solution are added, and the mixture is stirred for a further 12 h, evaporated and taken up in 1 N aqueous hydrochloric acid. It is washed with ethyl acetate, subjected to conventional working-up with sodium hydroxide solution/ethyl acetate to result in 1-[2-(N-p-carbamoyl-phenylacetyl-N-methylamino)-2-phenlylethyl]-3-hydroxy-pyrrolidine; Rf 0.12.

EXAMPLE 9

A solution of 10 g of 1-[2-(N-methyl-N-p-nitrophenylacetylamino)  -2-phenyl-ethyl]-3-hydroxy-pyrrolidine (Example 3) in 200 ml of methanol is hydrogenated at 20° and under atmospheric pressure on 5 g of Raney Ni until the calculated amount has been taken up. The mixture is filtered, and the filtrate is evaporated to result in 1-[2-(N-p-aminophenylacetyl-N-methyl-amino)-2-phenylethyl]-3-hydroxy-pyrrolidine ("A"), Rf 0.31.

The following compounds are obtained analogously by reduction of the corresponding nitro compounds:
1-[2-(N-p-aminophenylacetyl-N-methyl-amino)-2-phenylethyl ]-3R-hydroxy-pyrrolidine, Rf 0.31; [α]−2.9°; di-HCl' monohydrate, m.p. 61°
1-[2-(N-p-aminophenylacetyl-N-methyl-amino)-2-phenylethyl]-3S-hydroxy-pyrrolidine, Rf 0.31; [α]−2.9°;
1-[2S-(N-p-aminophenylacetyl-N-methyl-amino)-2-phenylethyl]-3S-hydroxy-pyrrolidine, Rf 0.31; [α]+121.5°; di-HCl' dihydrate, m.p. 232°
1-[2-(N-o-aminophenylacetyl-N-methyl-amino)-2-phenylethyl]-3-hydroxy-pyrrolidine
1-[2-(N-o-aminophenylacetyl-N-methyl-amino)-2-phenylethyl]-3R-hydroxy-pyrrolidine
1-[2-(N-o-aminophenylacetyl-N-methyl-amino)-2-phenylethyl]-3S-hydroxy-pyrrolidine
1-[2S-(N-o-aminophenylacetyl-N-methyl-amino)-2-phenylethyl]-3S-hydroxy-pyrrolidine, Rf 0.36; [α]+136.1°; di-HCl' dihydrate, m.p. 206°
1-[2-(N-m-aminophenylacetyl-N-methyl-amino)-2-phenylethyl]-3-hydroxy-pyrrolidine
1-[2-(N-m-aminophenylacetyl-N-methyl-amino)-2-phenylethyl]-3R-hydroxy-pyrrolidine
1-[2-(N-m-aminophenylacetyl-N-methyl-amino)-2-phenylethyl]-3S-hydroxy-pyrrolidine
1-[2S-(N-m-aminophenylacetyl-N-methyl-amino)-2-phenylethyl]-3-hydroxy-pyrrolidine
1-[2-(N-5-amino-2-thienyl-acetyl-N-methyl-amino)-2-phenyl-ethyl]-3-hydroxy-pyrrolidine
1-[2-(N-2-amino-3-chlorophenylacetyl-N-methyl-amino)-2-phenyl-ethyl]-3-hydroxy-pyrrolidine
1-[2-(N-2-amino-4-chlorophenylacetyl-N-methyl-amino)-2-phenyl-ethyl]-3-hydroxy-pyrrolidine
1-[2-(N-2-amino-5-chlorophenylacetyl-N-methyl-amino)-2-phenyl-ethyl]-3-hydroxy-pyrrolidine
1-[2-(N-2-amino-6-chlorophenylacetyl-N-methyl-amino)-2-phenyl-ethyl]-3-hydroxy-pyrrolidine 1-[2-(N-3-amino-2-chlorophenylacetyl-N-methyl-amino)-2-phenyl-ethyl]-3-hydroxy-pyrrolidine
1-[2-(N-3-amino-4-chlorophenylacetyl-N-methyl-amino)-2-phenyl-ethyl]-3-hydroxy-pyrrolidine
1-[2-(N-3-amino-5-chlorophenylacetyl-N-methyl-amino)-2-phenyl-ethyl]-3-hydroxy-pyrrolidine
1-[2-(N-3-amino-6-chlorophenylacetyl-N-methyl-amino)-2-phenyl-ethyl]-3-hydroxy-pyrrolidine
1-[2-(N-4-amino-2-chlorophenylacetyl-N-methyl-amino)-2-phenyl-ethyl]-3-hydroxy-pyrrolidine
1-[2-(N-4-amino-3-chlorophenylacetyl-N-methyl-amino)-2-phenyl-ethyl]-3-hydroxy-pyrrolidine
1-[2-(N-2-amino-3-bromophenylacetyl-N-methyl-amino)-2-phenyl-ethyl]-3-hydroxy-pyrrolidine
1-[2-(N-2-amino-4-bromophenylacetyl-N-methyl-amino)-2-phenyl-ethyl]-3-hydroxy-pyrrolidine
1-[2-(N-2-amino-5-bromophenylacetyl-N-methyl-amino)-2-phenyl-ethyl]-3-hydroxy-pyrrolidine
1-[2-(N-2-amino-6-bromophenylacetyl-N-methyl-amino)-2-phenyl-ethyl]-3-hydroxy-pyrrolidine
1-[2-(N-3-amino-2-bromophenylacetyl-N-methyl-amino)-2-phenyl-ethyl]-3-hydroxy-pyrrolidine
1-[2-(N-3-amino-4-bromophenylacetyl-N-methyl-amino)-2-phenyl-ethyl]-3-hydroxy-pyrrolidine
1-[2-(N-3-amino-5-bromophenylacetyl-N-methyl-amino)-2-phenyl-ethyl]-3-hydroxy-pyrrolidine
1-[2-(N-3-amino-6-bromophenylacetyl-N-methyl-amino)-2-phenyl-ethyl]-3-hydroxy-pyrrolidine
1-[2-(N-4-amino-2-bromophenylacetyl-N-methyl-amino)-2-phenyl-ethyl]-3-hydroxy-pyrrolidine
1-[2-(N-4-amino-3-bromophenylacetyl-N-methyl-amino)-2-phenyl-ethyl]-3-hydroxy-pyrrolidine.

EXAMPLE 10

3.53 g of "A" are dissolved in 175 ml of dichloromethane and, while stirring, a solution of 0.8 g of acetyl chloride in 10 ml of dichloromethane is added dropwise. The solution is stirred for 10 minutes and then concentrated, and the resulting 1-[2-(N-p-acetamidophenylacetyl -N-methyl-amino)-2-phenyl-ethyl]-3-hydroxy-pyrrolidine is filtered off. Rf 0.19.

The following are obtained analogously by acylation of the corresponding primary amino compounds:
1-[2-(N-p-acetamidophenylacetyl-N-methyl-amino)-2-phenylethyl]-3R-hydroxy-pyrrolidine, Rf 0.19; [α]−2.4° HCl' dihydrate, m.p. 125°
1-[2-(N-p-acetamidophenylacetyl-N-methyl-amino)-2-phenylethyl]-3S-hydroxy-pyrrolidine, Rf 0.19; [α]+2.4°
1-[2S-(N-p-acetamidophenylacetyl-N-methyl-amino)-2-phenylethyl]-3-hydroxy-pyrrolidine
1-[2S-(N-p-acetamidophenylacetyl-N-methyl-amino)-2-phenylethyl]-3S-hydroxy-pyrrolidine, Rf 0.19
1-[2-(N-o-acetamidophenylacetyl-N-methyl-amino)-2-phenylethyl]-3-hydroxy-pyrrolidine
1-[2-(N-o-acetamidophenylacetyl-N-methyl-amino)-2-phenylethyl]-3R-hydroxy-pyrrolidine
1-[2-(N-o-acetamidophenylacetyl-N-methyl-amino)-2-phenylethyl]-3S-hydroxy-pyrrolidine
1-[2S-(N-o-acetamidophenylacetyl-N-methyl-amino)-2-phenyl-ethyl]-3-hydroxy-pyrrolidine
1-[2S-(N-o-acetamidophenylacetyl-N-methyl-amino)-2-phenylethyl]-3S-hydroxy pyrrolidine, Rf 0.34
1-[2-(N-m-acetamidophenylacetyl-N-methyl-amino)-2-phenylethyl]-3-hydroxy-pyrrolidine
1-[2-(N-m-acetamidophenylacetyl-N-methyl-amino)-2-phenylethyl]-3R-hydroxy-pyrrolidine
1-[2-(N-m-acetamidophenylacetyl-N-methyl-amino)-2-phenylethyl]-3S-hydroxy-pyrrolidine
1-[2S-(N-m-acetamidophenylacetyl-N-methyl-amino)-2-phenyl-ethyl]-3-hydroxy-pyrrolidine
1-[2-(N-5-acetamido-2-thienyl-acetyl-N-methyl-amino)-2-phenyl-ethyl]-3-hydroxy-pyrrolidine
1-[2-(N-(3-acetamido-4-pyridylacetyl)-N-methyl-amino)-2-phenyl-ethyl]-3-hydroxy-pyrrolidine
1-[2-(N-(3-acetamido-4-methyl-2-pyridylacetyl)-N-methylamino) -2-phenyl-ethyl]-3-hydroxy-pyrrolidine
1-[2-(N-(5-acetamido-4-methyl-2-pyridylacetyl)-N-methylamino) -2-phenyl-ethyl]-3-hydroxy-pyrrolidine
1-[2-(N-methyl-N-m-trifluoromethylphenylacetyl-amino)-2-o-acetamidophenyl-ethyl]-3-hydroxy-pyrrolidine
1-[2-(N-methyl-N-m-trifluoromethylphenylacetyl-amino)-2-m-acetamidophenyl-ethyl]-3-hydroxy-pyrrolidine
1-[2-(N-methyl-N-m-trifluoromethylphenylacetyl-amino)-2-p-acetamidophenyl-ethyl]-3-hydroxy-pyrrolidine
1-[2-(N-methyl-N-o-methylsulfonylamino-phenylacetyl-amino) -2-phenyl-ethyl]-3-hydroxy-pyrrolidine
1-[2S-(N-methyl-N-o-methylsulfonylamino-phenylacetyl-amino)-2-phenyl-ethyl/-3S-hydroxy-pyrrolidine, Rf 0.51
1-[2-(N-methyl-N-m-methylsulfonylamino-phenylacetylamino)-2-phenyl-ethyl]-3-hydroxy-pyrrolidine
1-[2-(N-methyl-N-p-methylsulfonylamino-phenylacetylamino)-2-phenyl-ethyl]-3-hydroxy-pyrrolidine
1-[2-(N-methyl-N-5-methylsulfonylamino-2-thienylacetylamino)-2-phenyl-ethyl]-3-hydroxy-pyrrolidine
1-[2-(N-methyl-N-(3-methylsulfonylamino-4-pyridylacetyl)amino) -2-phenyl-ethyl-]-3-hydroxy-pyrrolidine 1-[2-(N-methyl-N-(3-methylsulfonylamino-4-methyl-2-pyridylacetyl) -amino)-2-phenyl-ethyl]-3-hydroxy-pyrrolidine
1-[2-(N-methyl-N-(5-methylsulfonylamino-4-methyl-2-pyridylacetyl) -amino)-2-phenyl-ethyl]-3-hydroxy-pyrrolidine
1-[2-(N-methyl-N-m-trifluoromethylphenylacetyl-amino)-2-o-methylsulfonylaminophenyl-ethyl]-3-hydroxy-pyrrolidine
1-[2-(N-methyl-N-m-trifluoromethylphenylacetyl-amino)-2-m-methylsulfonylaminophenyl-ethyl]-3-hydroxy-pyrrolidine
1-[2-(N-methyl-N-m-trifluoromethylphenylacetyl-amino)-2-p-methylsulfonylaminophenyl-ethyl]-3-hydroxy-pyrrolidine.

EXAMPLE 11

A mixture of 1 g of "A" and 10 ml of HCOOH is boiled for 2 h and then evaporated. Conventional workingup results in 1-[2-(N-p-formamidophenylacetyl-N-methylamino)-2-phenylethyl]-3-hydroxy-pyrrolidine.

The following are obtained analogously by formylation of the corresponding primary amino compounds:
1-[2-(N-p-formamidophenylacetyl-N-methyl-amino)-2-phenylethyl]-3R-hydroxy-pyrrolidine
1-[2-(N-p-formamidophenylacetyl-N-methyl-amino)-2-phenylethyl]-3-hydroxy-pyrrolidine
1-[2S-(N-p-formamidophenylacetyl-N-methyl-amino)-2-phenyl-ethyl]-3-hydroxy-pyrrolidine 1-[2-(N-o-formamidophenylacetyl-N-methyl-amino)-2-phenylethyl]-3-hydroxy-pyrrolidine
1-[2-(N-o-formamidophenylacetyl-N-methyl-amino)-2-phenylethyl]-3R-hydroxy-pyrrolidine
1-[2-(N-o-formamidophenylacetyl-N-methyl-amino)-2-phenylethyl]-3S-hydroxy-pyrrolidine
1-[2S-(N-o-formamidophenylacetyl-N-methyl-amino)-2-phenyl-ethyl]-3S-hydroxy-pyrrolidine
1-[2-(N-m-formamidophenylacetyl-N-methyl-amino)-2-phenylethyl]-3-hydroxy-pyrrolidine
1-[2-(N-m-formamidophenylacetyl-N-methyl-amino)-2-phenylethyl]-3R-hydroxy-pyrrolidine
1-[2-(N-m-formamidophenylacetyl-N-methyl-amino)-2-phenylethyl]-3S-hydroxy-pyrrolidine
1-[2S-(N-m-formamidophenylacetyl-N-methyl-amino)-2-phenyl-ethyl]-3S-hydroxy-pyrrolidine
1-[2-(N-5-formamido-2-phenylacetyl-N-methyl-amino)-2-phenyl-ethyl]-3-hydroxy-pyrrolidine
1-[2-(N-3-formamido-4-pyridylacetyl-N-methyl-amino)-2-phenyl-ethyl]-3-hydroxy-pyrrolidine
1-[2-(N-3-formamido-4-methyl-2-pyridylacetyl-N-amino)-2-phenyl-ethyl]-3-hydroxy-pyrrolidine
1-[2-(N-5-formamido-4-methyl-2-pyridylacetyl-N-amino)-2-phenyl-ethyl]-3-hydroxy-pyrrolidine
1-[2-(N-methyl-N-m-trifluoromethylphenylacetyl-amino)-2-o-formamidophenyl-ethyl]-3-hydroxy-pyrrolidine
1-[2-(N-methyl-N-m-trifluoromethylphenylacetyl-amino)-2-m-formamidophenyl-ethyl]-3-hydroxy-pyrrolidine
1-[2-(N-methyl-N-m-trifluoromethylphenylacetyl-amino)-2-p-formamidophenyl-ethyl]-3-hydroxy-pyrrolidine.

EXAMPLE 12

4.26 g of "A" dihydrochloride are dissolved in 50 ml of water, and 0.81 g of KCNO is added. After the mixture has been stirred at 20° for 3 h it is concentrated to result in 1-[2-(N-methyl-N-p-ureidophenylacetylamino)-2-phenyl-ethyl]-3-hydroxy-pyrrolidine, Rf 0.09.

The following are obtained analogously from the corresponding primary amines
1-[2-(N-methyl-N-p-ureidophenylacetyl-amino)-2-phenylethyl]-3R-hydroxy-pyrrolidine, Rf 0.09; [α]−2.7° HCl' trihydrate, m.p. 94°
1-[2-(N-methyl-N-p-ureidophenylacetyl-amino)-2-phenylethyl]-3S-hydroxy-pyrrolidine, Rf 0.09; [α]+2.7°
1-[2S-(N-methyl-N-p-ureidophenylacetyl-amino)-2-phenylethyl]-3-hydroxy-pyrrolidine, Rf 0.09; [α]+114.0°
1-[2-(N-methyl-N-o-ureidophenylacetyl-amino)-2-phenylethyl]-3-hydroxy-pyrrolidine
1-[2-(N-methyl-N-o-ureidophenylacetyl-amino)-2-phenylethyl]-3R-hydroxy-pyrrolidine
1-[2-(N-methyl-N-o-ureidophenylacetyl-amino)-2-phenylethyl]-3S-hydroxy-pyrrolidine
1-[2S-(N-methyl-N-o-ureidophenylacetyl-amino)-2-phenylethyl]-3-hydroxy-pyrrolidine, Rf 0.20; [α]+107.9° HCl' trihydrate, m.p. 151°
1-[2S-(N-methyl-N-o-ureidophenylacetyl-amino)-2-phenylethyl]-3S-hydroxy-pyrrolidine, Rf 0.20
1-[2-(N-methyl-N-m-ureidophenylacetyl-amino)-2-phenylethyl]-3-hydroxy-pyrrolidine
1-[2-(N-methyl-N-m-ureidophenylacetyl-amino)-2-phenylethyl]-3R-hydroxy-pyrrolidine
1-[2-(N-methyl-N-m-ureidophenylacetyl-amino)-2-phenylethyl]-3S-hydroxy-pyrrolidine
1-[2S-(N-methyl-N-m-ureidophenylacetyl-amino)-2-phenylethyl]-3-hydroxy-pyrrolidine
1-[2-(N-methyl-N-5-ureido-2-thienylacetyl-amino)-2-phenyl-ethyl]-3-hydroxy-pyrrolidine
1-[2-(N-methyl-N-3-ureido-4-pyridylacetyl-amino)-2-phenyl-ethyl]-3-hydroxy-pyrrolidine
1-[2-(N-methyl-N-3-ureido-4-methyl-pyridylacetyl-amino)-2-phenyl-ethyl]-3-hydroxy-pyrrolidine
1-[2-(N-methyl-N-5-ureido-4-methyl-pyridylacetyl-amino)-2-phenyl-ethyl]-3-hydroxy-pyrrolidine
1-[2-(N-methyl-N-m-trifluoromethylphenylacetyl-amino)-2-o-ureidophenyl-ethyl]-3-hydroxy-pyrrolidine
1-[2-(N-methyl-N-m-trifluoromethylphenylacetyl-amino)-2-m-ureidophenyl-ethyl]-3-hydroxy-pyrrolidine
1-[2-(N-methyl-N-m-trifluoromethylphenylacetyl-amino)-2-p-ureidophenyl-ethyl]-3-hydroxy-pyrrolidine.

EXAMPLE 13

A mixture of 5.53 g of "A", 0.57 g of methyl mixture is evaporated and subjected to conventional working-up to result in 1-[2-(N-methyl-N-p-(N'-methylureido)-phenylacetyl-amino)-2-phenyl-ethyl]-3-hydroxypyrrolidine.

The following are obtained analogously from the corresponding primary amines:
1-[2-(N-methyl-N-o-(N,-methyl-ureido)-phenylacetylamino)-2-phenyl-ethyl]-3-hydroxy-pyrrolidine
1-[2-(N-methyl-N-m-(N,-methyl-ureido)-phenylacetylamino)-2-phenyl-ethyl]-3-hydroxy-pyrrolidine
1-[2-(N-methyl-N-3-(N,-methylureido)-4-pyridylacetylamino)-2-phenyl-ethyl]-3-hydroxy-pyrrolidine
1-[2-(N-methyl-N-3-(N,-methylureido)-4-methyl-2-pyridylacetyl-amino) -2-phenyl-ethyl]-3-hydroxy-pyrrolidine
1-[2-(N-methyl-N-5-(N,-methylureido)-4-methyl-2-pyridylacetyl-amino) -2-phenyl-ethyl]-3-hydroxy-pyrrolidine.

EXAMPLE 14 a) Analogously to Example 1 1-[2S-(N-(4-methoxy-3-nitrophenylacetyl)-N-methyl-amino) -2-phenyl-ethyl]-3-S-hydroxy-pyrrolidine (Rf 0.44) is obtained from 1-(2S-methylamino-2 phenyl-ethyl)-3S-hydroxy-pyrrolidine and 4-methoxy-3-nitrophenylacetyl chloride.

b) By hydrogenation in analogy to Example 9, 1-[2S-(N-(3-amino-4-methoxy-phenylacetyl)-N-methyl-amino)-2-phenyl-ethyl]-3S-hydroxy-pyrrolidine (Rf 0.31) is obtained from the compound prepared according to a), The following Examples relate to pharmaceutical preparations containing amines of formula I or their acid addition salts:

Example A

Tablets

A mixture of 0.1 kg of 1-[2S-(N-o-aminophenylacetyl-N -methylamino)-2-phenyl-ethyl]-3-hydroxy-pyrrolidine dihydrochloride dihydrate, 4 kg of lactose, 1.2 kg of potato starch, 0.2 kg of talc and 0.1 kg of magnesium stearate is compressed to tablets in conventional manner such that each tablet contains 10 mg of active ingredient.

Example B

Coated tablets

Tablets are produced by compression analogously to Example A and are then covered in conventional manner with a coating of sucrose, potato starch, talc, tragacanth and colorant.

Example C

Capsules 2 kg of 1-2S-(N-methyl-N-o-ureidophenylacetylamino)-2-phenylethyl]-3-hydroxy-pyrrolidine hydrochloride dihydrate are filled into hard gelatin capsules in conventional manner such that each capsule contains 20 mg of active ingredient.

Example D

Ampoules

A solution of 1-[2S-(N-p-aminophenylacetyl-N-methylamino) -2-phenyl-ethyl]-3-hydroxy-pyrrolidine dihydrochloride dihydrate in 15 l of propane-1,2-diol and 15 l of double-distilled water is filtered under sterile conditions and filled into ampoules, and the ampoules are sealed under sterile conditions. Each ampoule contains 2 mg of active ingredient.

Tablets, coated tablets, capsules and ampoules which contain one or more of the other active ingredients of formula I and/or their physiologically compatible salts can be obtained in analogous manner.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 1-(2-arylethyl)-pyrrolidine of the formula I

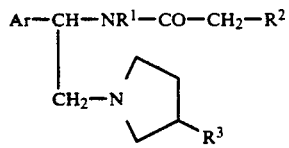

wherein
Ar is a phenyl group which is unsubstituted or monosubstituted by OH, —O—CO—NH$_2$, —O—CO—NHA, —O—CO—NA$_2$, NH$_2$, —NH—CHO, —NH—CO—A, —NH—CO—NH$_2$, —NH—CO—NHA or NH—SO$_2$—A, R$^1$ is A, R$^2$ is a phenyl, naphthyl, thienyl, benzothienyl or pyridyl group which is unsubstituted or mono- or disubstituted by A, Hal, CF$_3$, OH, OA, —O—CO—NH$_2$, —O—CO—NHA, —O—CO—NA$_2$, NO$_2$, NH$_2$, —NH—CHO, —NH—CO—A, —NH—CO—NH$_2$, —NH—CO—NHA, —NH—SO$_2$A, —CO—A, —CONH$_2$, —CONHA, —CONA$_2$, —CH$_2$—CONH$_2$ and/or —O—CH$_2$—CONH$_2$, R$^3$ is OH or CH$_2$OH, A is alkyl with 1–4 C atoms and Hal is F, Cl, Br or I, or a pharmaceutically acceptable salt thereof.

2. A compound according to claim 1 which is
a) 1-[2-(N-3,4-dichlorophenylacetyl-N-methylamino)-2-phenyl-ethyl]-3-hydroxy-pyrrolidine;
b) 1-[2-(N-3,4-dichlorophenylacetyl-N-methylamino)-2-phenyl-ethyl]-3-hydroxymethylpyrrolidine;
c) 1-[2-(N-methyl-N-p-nitrophenylacetyl-amino)-2-phenyl-ethyl]-3-hydroxy-pyrrolidine;
d) 1-[2-(N-p-aminophenylacetyl-N-methyl-amino)-2-phenyl-ethyl]-3-hydroxy-pyrrolidine;
e) 1-[2-(N-p-acetamidophenylacetyl-N-methylamino)-2-phenyl-ethyl]-3-hydroxy-pyrrolidine;
f) 1-[2-(N-methyl-N-p-ureidophenylacetyl-amino)-2-phenyl-ethyl]-3-hydroxy-pyrrolidine;
g) 1-[2-(N-o-aminophenylacetyl-N-methyl-amino)-2-phenyl-ethyl]-3-hydroxy-pyrrolidine;
h) 1-[2-(N-methyl-N-o-ureidophenylacetyl-amino)-2-phenyl-ethyl]-3-hydroxy-pyrrolidine; or
i) 1-[2-(N-m-aminophenylacetyl-N-methyl-amino)-2-phenyl-ethyl]-3-hydroxy-pyrrolidine
or a pharmaceutically acceptable salt thereof.

3. A compound of claim 1, wherein the halogen is chlorine or fluorine.

4. A compound of claim 1, wherein R$^1$ is methyl or ethyl.

5. A compound of claim 1, wherein R$^3$ is OH.

6. A compound of claim 1, wherein Rhu 3 is CH$_2$OH.

7. A compound of claim 1, wherein Ar is an unsubstituted phenyl group.

8. A compound of claim 1, wherein Ar is an substituted phenyl group in the p- or m-position.

9. A pharmaceutical preparation, comprising at least one compound of claim 1 and a pharmaceutically acceptable carrier.

10. A pharmaceutical preparation according to claim 9 having a dosage between 1 and 500 mg.

11. A 1(2-arylethyl)-pyrrolidine of claim 1, wherein Ar is phenyl; and
R$^2$ is phenyl, thienyl, naphthyl, or benzothienyl.

12. A method of treating pain comprising administering a compound of claim 1.

* * * * *